United States Patent [19]

Paucot

[11] 4,352,939
[45] Oct. 5, 1982

[54] CHLOROBROMODICARBOXYLIC ACIDS AND PROCESSES FOR THEIR MANUFACTURE AND THEIR USE

[75] Inventor: Andre Paucot, Brussels, Belgium
[73] Assignee: Solvay & Cie. (Societe Anonyme), Brussels, Belgium
[21] Appl. No.: 181,354
[22] Filed: Aug. 26, 1980
[30] Foreign Application Priority Data Aug. 27, 1979 [FR] France ................... 79 21629

[51] Int. Cl.³ ........................... C07C 69/753
[52] U.S. Cl. .................................. 560/120
[58] Field of Search ................ 560/120; 528/39.7
[56] References Cited
U.S. PATENT DOCUMENTS 3,869,502 3/1975 Papa ..................... 560/120

FOREIGN PATENT DOCUMENTS 1187999 4/1970 United Kingdom .

Primary Examiner—Michael L. Shippen
Attorney, Agent, or Firm—Spencer & Kaye

[57] ABSTRACT

The invention relates to diacids resulting from tetrahydrophthalic acid (chlorendic acid).

The diacids correspond to the formula

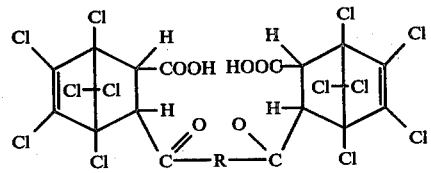

in which R represents the radical

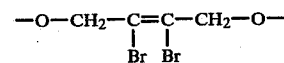

or the radical

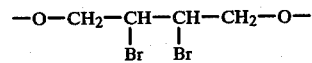

They are prepared using an excess of chlorendic acid.

They can be used as fireproofing additives for polymeric materials or as prepolymers for polycondensation reactions.

2 Claims, No Drawings

CHLOROBROMODICARBOXYLIC ACIDS AND PROCESSES FOR THEIR MANUFACTURE AND THEIR USE

BACKGROUND OF THE INVENTION

The present invention relates to chlorobromodicarboxylic acids resulting from the condensation of 2,3-dibromobut-2-ene-1,4-diol or 2,3-dibromobutane-1,4-diol with hexachloroendomethylenetetrahydrophthalic acid, which is commonly referred to as chlorendic acid. It also relates to processes for the manufacture of these products and their use as reactive or unreactive additives for fireproofing synthetic materials.

It is known, from French Pat. Nos. 1,502,049 and 1,502,050, filed Oct. 5th 1966 in the name of PRODUITS CHIMIQUES PECHINEY-SAINT-GOBAIN, to manufacture fireproof synthetic materials, such as crosslinked polyesters, or polyurethanes, starting from products resulting from the polycondensation of mixtures of polycarboxylic acids, which can be polysubstituted by halogen, with 2,3-dibromobut-2-ene-1,4-diol or 2,3-dibromobutane-1,4-diol, which is optionally mixed with another polyol. The diols and polycarboxylic acids are used in proportions such that the resulting polycondensate possesses an excess of alcohol groups, relative to the carboxyl groups. The polycondensates thus obtained have a serious disadvantage. In fact, they consist not of a single product with a well-defined formula, but of a mixture of products in which the composition and the nature of the constituents can vary as a function of the operating conditions used, and especially as a function of the excess of diol, and are very difficult to reproduce. Thus, these mixtures of polycondensates cannot be used in practice as fireproofing agents.

SUMMARY OF THE INVENTION

The object of the present invention is to provide chlorobromodicarboxylic acids which result from the condensation of 2,3-dibromobut-2-ene-1,4-diol or 2,3-dibromobutane-1,4-diol with a polyhalogenodicarboxylic acid, and which no longer exhibit this disadvantage.

For this purpose, the invention relates to chlorobromodicarboxylic acids corresponding to the formula

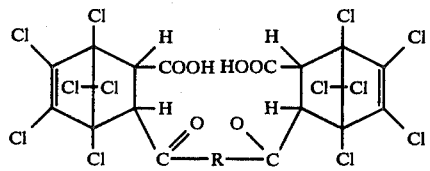

in which R represents the radical

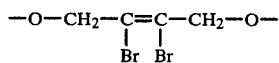

or the radical

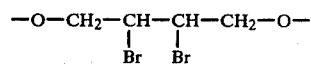

The preferred diacid according to the invention is that in which R represents the radical

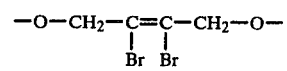

The melting point of this product is between 221° C. and 224° C., measured at atmospheric pressure.

The invention also relates to a process for the manufacture of diacids of the formula (I).

According to the prior art, the reaction of 2,3-dibromobut-2-ene-1,4-diol or 2,3-dibromobutane-1,4-diol with polycarboxylic acids, in relative amounts such that there is an excess of hydroxyl groups, leads to mixtures of polycondensates from which it would not be economic to separate the diesterified derivative, in the case where the latter was formed.

The process according to the invention makes it possible to obtain the diacids of the formula (I) in a substantially pure state and with yields exceeding 75%, relative to the amount of diol used.

The process according to the invention consists in reacting 2,3-dibromobut-2-ene-1,4-diol or 2,3-dibromobutane-1,4-diol with an excess of chlorendic acid.

DETAILED DESCRIPTION OF THE INVENTION

Usually, the amounts of chlorendic acid and diol used in the process of the present invention are such that the ratio of chlorendic acid to the diol is more than 2.2 mols per mol. Preferably, this ratio is chosen to be more than 2.5 and, in particular, the preferred ratios are ratios of more than 3. Generally, for economical reasons, molar ratios superior to 30 are not used.

The other parameters of the reaction of chlorendic acid with the diol are not in themselves critical and are choen such as are normal for this type of reaction. The reaction temperature is usually above 70° C. The reaction is preferably carried out at temperatures between 80° and 300° C. and more particularly between 90° and 180° C. The pressures are usually chosen between 0.1 and 50 bars. The reaction is preferably carried out at between 0.2 and 10 bars and more particularly at atmospheric pressure.

The reaction of chlorendic acid with the diol is generally carried out in a liquid medium. Apart from the reactants, this liquid medium preferably contains a solvent which is inert under the reaction conditions, or a mixture of such solvents. Organic solvents are normally used and the preferred organic solvents are those having a boiling point above 70° C. and more particularly between 90° and 180° C. Amongst the latter, halogenated aliphatic solvents and substituted or unsubstituted aromatic solvents are preferred. The most preferable category of solvents is the category of unsubstituted aromatic or alkylaromatic compounds, such as benzene, toluene, xylenes and their higher homologues. Very good results have been obtained with toluene.

Since the diesterification reaction is a reaction in which water is formed, any measure which makes it possible to remove the water of reaction can assist the formation of the products of the invention. A preferred embodiment of the process according to the invention consists in removing the water during the reaction by means of evaporation. Another embodiment consists in entraining the water with the solvent by means of distillation. In this case, the solvent can advantageously be toluene because it forms an azeotrope with water, and the azeotrope can be removed under the usual operating conditions for the reaction, as the reaction proceeds.

The order in which the chlorendic acid and the diol are introduced during the reaction is not critical.

If the process is carried out in a solvent medium, the total amount of chlorendic acid and diol used is normally chosen between 0.1 and 10% by weight of the total reaction mixture. This amount is preferably chosen between 0.2 and 5% by weight.

In order to accelerate the esterification reaction, it is possible to add, to the reaction mixture, a catalyst of the acid or basic type and also compounds known for their water-binding properties. Catalysts which are advantageously used are Lewis or Bronsted acids and more particularly protonic acids. Amongst the latter, the preferred acids are strong acids, such as hydrochloric acid or sulphuric acid, and derivatives thereof. Very particularly, it is preferred to carry out the reaction with sulphuric acid derivatives, and, amongst these, the preferred catalyst is para-toluenesulphonic acid.

The amount of catalyst used is normally between 0.1 and 5% by weight, calculated relative to the diol. The preferred amount of catalyst is between 0.2 and 1% by weight of diol.

Once the esterification reaction has ended, the diester formed can easily be separated from the residual reactants and the reaction solvent. Any known physical or chemical means can be used for this purpose. Preferably, all the solvent which may be present is first evaporated off and the chlorendic acid and the residual diols are then extracted with hot water, in which all the unconverted reactants are soluble. The residual solid substantially consists of diacid of the formula (I).

The temperature of the extraction water is usually chosen between 60° and 100° C. and preferably between 80° and 95° C. The diacid, which is not soluble in hot water, is obtained in the form of a solid precipitate which can easily be dried.

The process for the manufacture of diacids of the formula (I) can be applied to a mixture of 2,3-dibromobut-2-ene-1,4-diol and 2,3-dibromobutane-1,4-diol. However, it is preferred to use only one diol and more particularly 2,3-dibromobut-2-ene-1,4-diol.

The present invention also relates to a process for using diacids of the formula (I) as additives for fireproofing synthetic materials.

Thus, the diacids of the formula (I) can be used as unreactive additives in the majority of synthetic materials requiring an improvement in their fireproofing properties. This possibility results from the overall physical and chemical properties of these diacids, these properties being such that the migration of the diacids remains minimal, even under extreme conditions of use of the synthetic materials. Examples which may be mentioned of synthetic materials to which the diacids can advantageously be added are polyolefine resins, such as polyethylene and polypropylene, vinyl resins, such as polyvinyl chloride, acrylic resins, such as polymethyl methacrylate, styrene resins, such as polystyrene, polyamides, and saturated polyesters, such as poly(ethylene glycol) terephthalate.

The diacids of the formula (I) can also be used as reactive fireproofing additives which, by means of the carboxyl groups, enter into the structure of the molecule of the base compound of the synthetic material. For this use, which is preferred, the diacids of the formula (I) act as a monomer or a prepolymer, which contains a large amount of chlorine and bromine and which can participate in all the polycondensation reactions which usually involve monomers or prepolymers containing carboxyl groups. Thus, the diacids of the formula (I) can be used to manufacture polyesters, polyethers, polyurethanes, polyisocyanurates and other similar polymers which possess an enhanced fire resistance and heat resistance and are perfectly reproducible.

The following examples are given in order to illustrate the invention.

EXAMPLE 1

1.5 liters of toluene, 38.8 g (0.100 mol) of chlorendic acid, 6.15 g (0.025 mol) of 2,3-dibromobut-2-ene-1,4-diol and 0.2 g of para-toluenesulphonic acid are introduced into a 2 liter round-bottomed flask equipped with a condenser. The reaction mixture is then heated under reflux for 24 hours, the water formed being removed continuously in the form of an azeotrope with the toluene.

The mixture is then cooled and washed with cold water. The toluene in the organic phase is then removed by evaporation to dryness and this yields 39 g of a solid residue.

32 g of the solid residue are extracted with hot water at 90° C. in a Soxhlet apparatus for 48 hours, in order to remove the unreacted chlorendic acid and unreacted 2,3-dibromobut-2-ene-1,4-diol. The residual product is dried to constant weight in an oven at 200° C., the final weight being 15.5 g.

Physical analyses of this product show that it starts to melt at 221° C. and that melting ends at 223.5° C. Nuclear paramagnetic resonance analysis of the methyl ester of the resulting product makes it possible to conclude that the product is the diacid of the formula

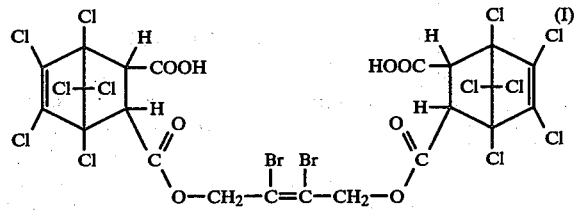

This is also confirmed by measuring the molecular weight by means of ebullioscopy in tetrahydrofurane, which gives a value of 902, the theoretical value being 988.

The yield of the reaction, calculated relative to the diol, is 76%, based on the theoretical molecular weight.

EXAMPLE 2

This example is given by way of comparison.

The reaction is carried out under conditions identical to those described in Example 1, but starting from 12.3 g (0.050 mol) of 2,3-dibromobut-2-ene-1,4-diol.

Chromatographic analyses carried out on the resulting product show that the product is a mixture of numerous compounds, including the unreacted reactants and several unidentified esters.

EXAMPLE 3

This example is also given by way of comparison.

The reaction is again carried out under conditions described in Example 1, but starting from 19.4 g (0.05 mol) of chlorendic acid and 24.6 g (0.100 mol) of 2,3-dibromobut-2-ene-1,4-diol.

Chromatographic analyses carried out on the resulting product show that the proportion of unidentified esters obtained is larger than in Example 2.

From a comparison of Examples 1, 2 and 3, it can be concluded that the process in which the reaction is carried out with an excess of chlorendic acid is the only process which makes it possible to obtain a single compound in the substantially pure state.

I claim:

1. Chlorobromodicarboxylic acid which corresponds to the formula

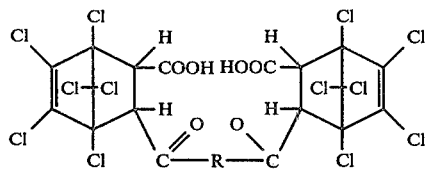

in which R represents the radical

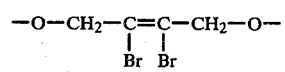

or the radical

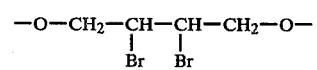

2. Diacid according to claim 1, wherein R represents the radical

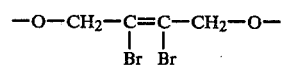

* * * * *